US012806128B2

United States Patent
(12) United States Patent
Jiang et al.

(10) Patent No.: US 12,806,128 B2
(45) Date of Patent: Nov. 24, 2026

(54) GEL COMPOSITION, THE PREPARATION METHOD AND THE USE OF THE SAME

(71) Applicant: BASF SE, Ludwigshafen (DE)

(72) Inventors: Zhi Ting Jiang, Shanghai (CN); Long Zhao, Shanghai (CN); Yu Ting Xu, Shanghai (CN); Yi Yao Wang, Shanghai (CN)

(73) Assignee: BASF SE, Ludwigshafen am Rhein (DE)

(*) Notice: Subject to any disclaimer, the term of this patent is extended or adjusted under 35 U.S.C. 154(b) by 274 days.

(21) Appl. No.: 18/706,443

(22) PCT Filed: Oct. 18, 2022

(86) PCT No.: PCT/EP2022/078950
§ 371 (c)(1),
(2) Date: May 1, 2024

(87) PCT Pub. No.: WO2023/078671
PCT Pub. Date: May 11, 2023

(65) Prior Publication Data

US 2026/0157949 A1 Jun. 11, 2026

(30) Foreign Application Priority Data

Nov. 5, 2021 (WO) ................ PCT/CN2021/129073

(51) Int. Cl.

| | |
|---|---|
| ***A61K 8/60*** | (2006.01) |
| ***A61K 8/06*** | (2006.01) |
| ***A61K 8/34*** | (2006.01) |
| ***A61Q 19/00*** | (2006.01) |

(52) U.S. Cl.
CPC ................ *A61K 8/604* (2013.01); *A61K 8/06* (2013.01); *A61K 8/345* (2013.01); *A61Q 19/00* (2013.01); *A61K 2800/10* (2013.01); *A61K 2800/48* (2013.01)

(58) Field of Classification Search
None
See application file for complete search history.

(56) References Cited

U.S. PATENT DOCUMENTS

| | | | |
|---|---|---|---|
| 6,248,792 | B1 | 6/2001 | Lazarowitz |
| 6,524,594 | B1 | 2/2003 | Santora et al. |

FOREIGN PATENT DOCUMENTS

| | | | | |
|---|---|---|---|---|
| EP | 1917954 A1 | | 5/2008 | |
| EP | 2881381 A1 | | 6/2015 | |
| EP | 3369415 A1 | | 9/2018 | |
| WO | WO-2013/076691 A1 | | 5/2013 | |
| WO | WO-2014/098265 A1 | | 6/2014 | |
| WO | WO-2018/114406 A1 | | 6/2018 | |
| WO | WO 2018/158215 A1 | * | 9/2018 | ............... A61Q 1/14 |
| WO | WO-2021/052398 A1 | | 3/2021 | |

OTHER PUBLICATIONS

International Search Report for PCT Patent Application No. PCT/CN2021/129073, Issued on May 2, 2022, 4 pages.
International Search Report for PCT Patent Application No. PCT/EP2022/078950, Issued on Apr. 3, 2023, 4 pages.

* cited by examiner

*Primary Examiner* — Brian J Davis
(74) *Attorney, Agent, or Firm* — Faegre Drinker Biddle & Reath LLP

(57) ABSTRACT

The present invention provides a cosmetic composition in the form of a transparent gel, comprising (a) an oil phase; (b) an emulsifier portion comprising at lease one carboxylated alkyl polyglycoside, at least one alkyl polyglycoside and at least one polyglyceryl esters; (c) an aqueous phase; and (d) at least one $C_2$-$C_6$ polyol; wherein said composition is in the form of a transparent gel, and wherein the oil phase is free from mineral oil and silicone oil. Also provided is the method for preparing the cosmetic composition and the use thereof. The cosmetic composition of the present invention has high oil content, superior stability and desirable cleansing efficacy.

17 Claims, No Drawings

GEL COMPOSITION, THE PREPARATION METHOD AND THE USE OF THE SAME

CROSS-REFERENCE TO RELATED APPLICATIONS

This is the U.S. national phase of International Application No. PCT/EP2022/078950, filed Oct. 18, 2022, which claims the benefit of International Patent Application No. PCT/CN2021/129073, filed Nov. 5, 2021.

FIELD OF THE INVENTION

The present invention relates to a transparent gel composition with high oil content which is free from ethoxylated emulsifiers, the preparation method and the uses thereof.

BACKGROUND

There are many different types of makeup compositions in the prior art. Generally, these compositions are classified into two categories: anhydrous or oil-based and water-based. The conventional anhydrous or oil-based makeup remover system has two advantages over the water-based system. First, the anhydrous or oil-based system is usable and effective on all makeup products on the market, both water rinsable and waterproof. The second advantage of the anhydrous or oil-based makeup remover system is that such a system does not necessarily require the addition of preservatives to prevent microorganism growth.

Various problems have been encountered in the prior art in formulating an an oil-based composition. These problems include, for example, producing a makeup remover composition which, when removed from the skin, does not leave behind a greasy or oily film or feel. Another disadvantage of the compositions found in the prior art is that such compositions have a tendency to be unstable in areas of high temperature.

In the cosmetics and personal care product market, the currently existing products, such as makeup removers, are mainly classified into three types of texture, like liquid (including water base and oil base), emulsion and gel. For gel format with high oil content, it has been popular in personal care and cosmetics industry, because they can overcome some drawbacks or limitations of the liquid oil formulations, such as the inconvenience owing to the high flowability during use on skin.

To achieve the purposes of easy use and desirable stability, the currently available gel products with high oil content are usually thickened by oil phase thickeners. Nevertheless, gel products obtained by using oil phase thickeners, have such problems as poor spreadability, unpleasant sensory feeling including an oily and sticky feeling of heaviness, and retention of an oil film on the skin. A stable gel product can be produced by adding gelling agent or thickening polymer (also known as polymeric thickener). For example, U.S. Pat. No. 6,524,594B1 discloses a gelled oil composition comprising an emulsifier, a gelling agent, an oil and a surfactant. It discloses that the gelling agent accounts for from about 3% to about 10% and preferably from about 3.5% to about 5.5%, based on the total weight of the composition. The gelling agent disclosed in U.S. Pat. No. 6,524,594B1 is selected from dextrin myristate, dextrin palmitate, a blend of at least two different polymer members selected from the group consisting of diblock copolymers, triblock copolymers, radical block copolymers and multiblock copolymers, or a mixture thereof. The presence of the gelling agent or the polymeric thickener in the above-disclosed gel products makes them less spreadable and not pleasant after being applied to the skin. Another feasible method to get high oil load emulsion is using D-phase emulsification technology. The product always tends to be unstable.

To solve the issue, some patents published their approach to make it milk-white cream, but it is not commercially attractive for consumers. Besides, polyoxyethylene (EO) emulsifier was known to form oil gel by D-phase emulsification. WO 2021052398A1 discloses the combination of two kind of non-ionic surfactants, alkyl polyglycosides and polyoxyalkylene alkyl ethers or polyoxyethylene fatty acid glyceryl esters, can make a stable oil gel-like appearance. This gel composition is free of polymeric thickener, gelling agent or thickening polymer, but contains polyoxyalkylene alkyl ethers or polyoxyethylene fatty acid glyceryl esters in the composition, which causes the concerns due to the presence of 1,4-dioxane contained as by-product, which is reported to have potential carcinogenicity. The use of ethoxylated emulsifiers for cosmetic and pharmaceutical uses is problematic since they are suspected of making the skin permeable to harmful substances and of forming undefined, possibly harmful substances under the action of UV. So the challenge is to obtain stable, transparent, and easy to spread gel products with high oil content without use of ethoxylated emulsifiers.

It thus remains a challenge to obtain a gel composition with high oil content, which is free from ethoxylated emulsifier and polymeric thickener and can still bring about satisfied transparency and stability, and can also achieve excellent make-up removal efficacy.

SUMMARY OF THE INVENTION

In the process of developing stable and attractive personal care products, which overcome at least one of the above-mentioned problems with the current personal care products, the inventors have surprisingly found that the combination of the following emulsifiers—carboxylated alkyl polyglycoside (also referred to "carboxylated APG"), alkyl polyglycosides (also referred to "APG"), and polyglyceryl esters—will give an high oil emulsion with transparent gel appearance, which is stable, attractive to consumers, and easy to package and transport.

Moreover, the gel composition of the present invention can be free or substantially free of polymeric thickener, gelling agent or thickening polymer. In particular, the gel composition of the present invention, is free from ethoxylated emulsifier which is required to be included in a gel composition with high oil content as reported in the prior art. Despite the absence or substantial absence of polymeric thickener, gelling agent, thickening polymer or ethoxylated emulsifier, the gel composition of the present invention with high oil content still have superior transparency and stability, when being applied and desirable cleansing efficacy.

In one aspect, the present invention provides a cosmetic composition, comprising (a) an oil phase;

(b) an emulsifier portion comprising at lease one carboxylated alkyl polyglycoside, at least one alkyl polyglycoside and at least one polyglyceryl ester;

(c) an aqueous phase; and (d) at least one $C_2$-$C_6$ polyol;

wherein said composition is in the form of a transparent gel, and wherein the oil phase is free from mineral oil and silicone oil.

In another aspect, the cosmetic composition of the present invention is free of or substantial free of ethoxylated emulsifier.

In another aspect, the present invention provides a method for preparing the above-mentioned cosmetic composition, comprising the following steps:

(a) adding the emulsifier portion, the $C_2$-$C_6$ polyol to the aqueous phase, and mixing—optionally and preferably with heating, stirring or simultaneous heating and stirring them uniformly;

(b) heating the oil phase;

(c) adding the oil phase obtained in step (b) into the aqueous phase obtained in step (a) under stirring; and (d) cooling the mixture obtained in step (c) under stirring to give a gel.

In a third aspect, the present invention provides use of the above-mentioned cosmetic composition for the preparation of personal care products.

In a fourth aspect, the present invention provides a method for personal care or cleansing, comprising the step of applying the cosmetic composition of the present invention to a desired location on the skin or hair in the presence of water, and then rinsing off the composition from the skin or hair with water.

The cosmetic composition of the present invention is in the form of a transparent gel, which is attractive to consumers. Particularly, the present composition is free from ethoxylated emulsifier. Moreover, the cosmetic composition in the gel form of the present invention has superior stability, although it has high level of oil.

As the cosmetic composition of the present invention is in the form of a transparent gel, it may also be referred to as "gel composition(s) of the present invention", "gel product(s) of the present invention" or "gel(s) of the present invention". These terms will be used interchangeably throughout the present description and the appended claims.

The aspects of the present invention will become apparent from the detailed description provided hereinafter. It should be understood that the detailed description and the specific examples, while indicating the preferred embodiment of the present invention, are intended for purposes of illustration only and are not intended to limit the scope of the present invention.

DETAILED DESCRIPTION OF THE INVENTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. Unless otherwise specified, all percentages and amounts expressed herein and elsewhere in the description should be understood to refer to percentages by weight. For example, the symbol "% by weight" means percentages by weight of the total composition. The amounts given are based on the active weight of the material.

As used herein, the term "transparency" refers to inventive cosmetic composition which has translucent or transparent light transmitting properties, and refers to a clear body which has the property of transmitting light without appreciable scattering, so that objects beyond are entirely visible.

As used herein, the terms "free of", "substantially free of", "free from", and/or "substantially free from" refer to compositions completely lacking the component or having such a small amount of the component that the component may be present less than 0.5% by weight, or less than 0.1% by weight or less than 0.01% by weight.

In one aspect, the present invention provides a cosmetic composition, comprising (a) an oil phase;

(b) an emulsifier portion comprising at lease one carboxylated alkyl polyglycoside, at least one alkyl polyglycoside and at least one polyglyceryl ester;

(c) an aqueous phase; and (d) at least one $C_2$-$C_6$ polyol;

wherein said composition is in the form of a transparent gel, and wherein the oil phase is free from mineral oil and silicone oil.

Preferably, the cosmetic composition of the present invention is free or substantial free from the ethoxylated emulsifier.

In an embodiment, based on the total weight of the cosmetic composition, (1) the oil phase may be present in an amount of from 50 to 90% by weight, such as from 55 to 89% by weight, from 60 to 88% by weight, from 65 to 87%, from 70 to 86%, from 75 to 85% by weight;

(2) the emulsifier portion comprising at lease one carboxylated alkyl polyglycoside, at least one alkyl polyglycoside and at least one polyglyceryl ester may be present in an amount of from 1 to 20% by weight, such as from 1.5 to 18% by weight, from 2 to 16% by weight, from 2.5 to 14% by weight, from 3 to 12% by weight, from 3.5 to 10% by weight, from 4 to 9% by weight, from 4.5 to 8.5% by weight, from 4.5 to 8% by weight, from 5 to 7.5% by weight, from 5 to 7% by weight;

(3) the aqueous phase may be present in an amount of from 1 to 15% by weight, such as from 2 to 12% by weight, from 3 to 11% by weight, from 4 to 10% by weight, from 5 to 10% by weight, from 6 to 10% by weight; and (4) the $C_2$-$C_6$ polyol may be present in an amount of from 1 to 15% by weight, such as from 2 to 12% by weight, from 3 to 10% by weight, from 4 to 10% by weight, and from 5 to 10% by weight.

The viscosity of the composition of the present invention depends on the specific application. Usually, the composition of the present invention has a viscosity at 25 °C of from 5,000 to 500,000 mPas, preferably 10,000 to 300,000 mPas, more preferably 20,000 to 250,000 mPas, in particular 35,000 to 200,000 mPas. Viscosity can be determined by rotational method and obtained at 23 °C using a Brookfield viscometer DV2T (spindle #7, rotational speed as 10 rpm).

In an embodiment, in the emulsifier portion, the at least one carboxylated alkyl polyglycoside and the at least one alkyl polyglycoside may be present at a weight ratio in the range of 1:6 to 6:1, preferably in the range 1:4 to 4:1, preferably in the range of 1:3 to 3:1, more preferably in the range of 1:2 to 3:1, still more preferably in the range of 3:4 to 5:2.

In an embodiment, in the emulsifier portion, the emulsifiers may be present at a weight ratio of the sum of the at least one carboxylated alkyl polyglycoside and the at least one alkyl polyglycoside to the at least one polyglyceryl ester in the range of 9:1 to 1:9, such as in the range of 8:2 to 2:8, in the range of 7:3 to 3:7, or in the range of 6:4 to 4:6, and particularly at the weight ratio of 9:1, 8:2, 7:3, 6:4, 5:5, 4:6, 3:7, 2:8 or 1:9. In addition, the emulsifiers may be present at a weight ratio of the sum of the at least one carboxylated alkyl polyglycoside and the at least one alkyl polyglycoside to the at least one polyglyceryl ester in any sub-range within the above ranges or in any sub-range having the above specific ratio values as the terminus, such as in the range of 9:1 to 2:8, in the range of 9:1 to 3:7, in the range of 9:1 to 4:6, in the range of 9:1 to 5:6, in the range of 9:1 to 5:5, in the range of 9:1 to 6:4, in the range of 9:1 to 7:3, in the range of 8:2 to 1:9, in the range of 8:2 to 3:7, in the range of 8:2 to 4:6, in the range of 8:2 to 5:5, in the range of 8:2 to 6:4, in the range of 8:2 to 7:3, in the range of 7:3 to 1:9, in the range of 7:3 to 2:8, in the range of 7:3 to 4:6, in the range of 7:3 to 5:5, in the range of 7:3 to 6:4, in the range of 6:4 to 1:9, in the range of 6:4 to 2:8, in the range of 6:4 to 3:7, in the range of 6:4 to 5:5, in the range of 5:5 to 1:9, in the range of 5:5 to 2:8, in the range of 5:5 to 3:7, in the range of 5:5 to 4:6, in the range of 4:6 to 1:9, in the range of 4:6 to 2:8, in the range of 4:6 to 3:7, in the range of 3:7 to 1:9, in the range of 3:7 to 2:8, or in the range of 2:8 to 1:9. Particularly, the emulsifiers are present at a weight ratio of the sum of the at least one carboxylated alkyl polyglycoside and the at least one alkyl polyglycoside to the at least one polyglyceryl ester in the range of 9:1 to 1:3, or 9:1 to 2:3, or more preferably in the range of 9:1 to 5:6, or more preferably in the range of 9:2 to 5:6.

Alkyl Polyglycoside

In an embodiment, the alkyl polyglycoside is of a formula (I):

$$R_1—O—(R_2—O)_a—(Z)_b—H \quad (I)$$

wherein $R_1$ is a straight chain or branched $C_6$-$C_{24}$-hydrocarbyl, $R_2$ is a straight chain $C_2$-$C_4$-alkylene, a is a number in the range of 0 to 10, preferably 0 to 4, Z is a residue of a reducing sugar having 5 to 6 carbons, and b is a number in the range of 1 to 5, preferably 1 to 2.

Alkyl polyglycosides can be produced by any well-known method to person skilled in the art, for example, by reacting a suitable carbohydrate with a fatty alcohol.

In above formula (I), $R_1$ is preferably a straight chain or branched $C_8$-$C_{18}$-alkyl, $C_{10}$-$C_{16}$-alkyl or $C_{12}$-$C_{14}$ alkyl for example n-octyl, n-nonyl, n-decyl, n-undecyl, n-dodecyl, n-tridecyl, n-tetradecyl, n-pentadecyl, n-hexadecyl, heptadecyl or octadecyl. Additionally, or alternatively, Z is a residue of a reducing sugar selected from glucose, fructose, galactose, xylose or arabinose, preferably glucose.

Preferably, in above formula (I), a is 0 and b is 1. Particularly, notable alkyl polyglycoside for the present invention are $C_8$-$C_{18}$ alkyl polyglycoside, for example decyl glucoside and lauryl glucoside, cetearyl glucoside, stearyl glucoside, cocyl glucoside, isostearyl glucoside, oleyl glucoside.

Carboxylated Alkyl Polyglycoside

In an embodiment, the carboxylated alkyl polyglycoside emulsifier is of a formula (II):

$$R_3—O—(R_4—O)_m—(S)_n—CH_2COO^-X^+ \quad (II)$$

wherein $R_3$ is a straight chain or branched $C_6$-$C_{24}$-hydrocarbyl, $R_4$ is straight chain $C_2$-$C_4$-alkylene, m is a number in the range of 0 to 10, preferably 0 to 4, S is a residue of a reducing sugar having 5 to 6 carbons, and n is a number in the range of 1 to 5, preferably 1 to 2, and X is an alkali metal ion.

In above formula (II), $R_3$ is preferably a straight chain or branched $C_8$-$C_{18}$ alkyl, preferably straight chain $C_{10}$-$C_{16}$ or $C_{12}$-$C_{14}$ alkyl, for example n-octyl, n-nonyl, n-decyl, n-undecyl, n-dodecyl, n-tridecyl, n-tetradecyl, n-pentadecyl, n-hexadecyl, heptadecyl or octadecyl, more preferably n-dodecyl (lauryl). Additionally, or alternatively, S is a residue of a reducing sugar selected from glucose, fructose, galactose, xylose or arabinose, preferably glucose.

More particularly preferred carboxylated alkyl polyglycoside and the method of preparation of the carboxylated alkyl polyglycoside can be found in U.S. Pat. No. 6,248,792 by reference.

The carboxylated alkyl polyglycoside emulsifiers possess anionic properties. They provide superior levels of stable foam and act as viscosity builder when used in various types of detergent compositions.

A variety of carboxylated alkyl polyglycoside emulsifiers can be used in the composition of the present invention. The carboxylated alkyl polyglycosides can be made by such methods as the reaction of an alkyl polyglycoside with an alpha- or 2-halocarboxylic acid such as 2-chloroacetic acid, or by the reaction of an alkyl polyglycoside with an alpha, beta-unsaturated carboxylic acid such as acrylic acid or methacrylic acid, or by the reaction of an alkyl polyglycoside with a cyclic carboxylic acid anhydride such as succinic anhydride or maleic anhydride. The carboxylated alkyl polyglycoside can be therefore the reaction product of an alkyl polyglycoside with an alpha- or 2-halocarboxylic acid; the reaction product of an alkyl polyglycoside with an alpha, beta-unsaturated carboxylic acid; or the reaction product of an alkyl polyglycoside with a cyclic carboxylic acid anhydride.

Particularly preferred carboxylated alkyl polyglycoside emulsifiers are those of formula (II) where $R_3$ is a straight chain or branched $C_8$-$C_{16}$ hydrocarbyl, S is a residue of a reducing sugar selected from glucose, fructose, galactose, xylose or arabinose glucose residue, preferably glucose, n is about 1.4 to 2, preferably 1.4 to 1.6, more preferably 1.55, m is zero. Preferably, in above formula (II), m is 0, and n is 1.

In an embodiment, the carboxylated alkyl polyglycoside emulsifiers may be at least one selected from the group consisting of $C_8$-$C_{10}$ alkyl glucose carboxylates, $C_8$-$C_{16}$ alkyl glucose carboxylates, $C_{12}$-$C_{16}$ alkyl glucose carboxylates, $C_9$-$C_{11}$ alkyl glucose carboxylates, $C_{12}$-$C_{20}$ alkyl glucose carboxylates, and a combination thereof, especially their sodium, magnesium, ammonium and mono-, di- and tri-thanolamine salts. More particularly, the alkyl glucose carboxylate may be at least one selected from the group consisting of sodium decyl glucose carboxylate, sodium lauryl glucose carboxylate, ammonium decyl glucose carboxylate, ammonium lauryl glucose carboxylate, and a combination thereof. One suitable carboxylated alkyl polyglycoside for the present invention is sodium lauryl glucose carboxylate which is commercially available from BASF under the tradename Plantapon® LGC Sorb.

In some preferred embodiments, in the composition according to the present invention, the alkyl polyglycoside emulsifier and the carboxylated alkyl polyglycoside emulsifier are used as a mixture.

In an embodiment, the alkyl polyglycoside may be at least one selected from the group consisting of $C_8$-$C_{10}$ alkyl polyglycosides, $C_8$-$C_{16}$ alkyl polyglycosides, $C_{12}$-$C_{16}$ alkyl polyglycosides, $C_9$-$C_{11}$ alkyl polyglycosides, $C_{12}$-$C_{20}$ alkyl polyglycosides, and a combination thereof. More particularly, the alkyl polyglycoside may be at least one selected from the group consisting of decyl glucoside, arachidyl glucoside, caprylyl/capryl glucoside, cetearyl glucoside, coco-glucoside, lauryl glucoside, and a combination thereof.

In an embodiment, the alkyl polyglycoside may be commercially available, for example as APG®, GLUCOPON®, or PLANTAREN® emulsifiers from BASF, or PLANTAPON® or PLANTACARE® emulsifiers from BASF. Examples of such emulsifiers may include but are not limited to: GLUCOPON® 225DK Emulsifier—an alkyl polyglycoside in which the alkyl group contains 8 to 10 carbon atoms and having an average degree of polymerization of 1.7; GLUCOPON® 425N Emulsifier—an alkyl polyglycoside in which the alkyl group contains 8 to 16 carbon atoms, having an average of 10.3 carbon atoms, and having an average degree of polymerization of 1.5; GLUCOPON® 625UP Emulsifier—an alkyl polyglycoside in which the alkyl group contains 12 to 16 carbon atoms and having an average degree of polymerization of 1.6; APG® 325N Emulsifier—an alkyl polyglycoside in which the alkyl group contains 9 to 11 carbon atoms and having an average degree to polymerization of 1.5; GLUCOPON® 600UP Emulsifier—an alkyl polyglycoside in which the alkyl group contains 12 to 16 carbon atoms and having an average degree of polymerization of 1.4; PLANTAREN® 2000 Emulsifier—a $C_8$-$C_{16}$ alkyl polyglycoside in which the alkyl group contains 8 to 16 carbon atoms and having an average degree to polymerization of 1.5; PLANTAREN® 1300 Emulsifier—a $C_{12}$-$C_{16}$ alkyl polyglycoside in which the alkyl group contains 12 to 16 carbon atoms and having an average degree to polymerization of 1.6; GLUCOPON® 220N Emulsifier—an alkyl polyglycoside in which the alkyl group contains 8 to 10 carbon atoms and having an average degree of polymerization of 1.5; PLANTACARE® 818 UP Emulsifier—a $C_8$-$C_{18}$ fatty alcohol glucoside, Coco-glucoside (INCI); PLANTACARE® 818 UP/MB* Emulsifier—a $C_8$-$C_{16}$ fatty alcohol glucoside, Mass Balance, Coco-glucoside (INCI); PLANTACARE® 1200 UP Emulsifier—a $C_{12}$-$C_{16}$ fatty alcohol glucoside, lauryl glucoside (INCI); PLANTACARE® 1200 UP/MB* Emulsifier—a $C_{12}$-$C_{16}$ fatty alcohol glucoside, lauryl glucoside (INCI); PLANTACARE® 2000 UP Emulsifier—a $C_8$-$C_{16}$ fatty alcohol glucoside, decyl glucoside (INCI); PLANTACARE® 2000 UP/MB* Emulsifier—a $C_8$-$C_{16}$ fatty alcohol glucoside, Mass Balance, decyl glucoside (INCI); PLANTACARE® 810 UP Emulsifier—a $C_8$-$C_{10}$ fatty alcohol glucoside, caprylyl/capryl glucoside (INCI); and PLANTAPON® LGC sorb Emulsifier—sodium lauryl glucose carboxylate (15-25%), lauryl glucoside (10-20%) and water (60-70%), from BASF.

Polyglyceryl Ester

In an embodiment, the polyglyceryl ester is at least one selected from the group consisting of polyglycerin fatty acid ester, polyglyceryl di-fatty acid ester and polyglyceryl di-polyhydroxy fatty acid ester.

Preferred polyglycerin fatty acid esters are any polyglyceryl-n fatty acid esters in which the fatty acid moiety is independently derived from a saturated or olefinically unsaturated, straight or branched chain fatty acid containing from 6 to 22 carbon atoms, preferably from 8 to 18 carbon atoms, or preferably from 12 to 18 carbon atoms, such as polyglyceryl-10 laurate, polyglyceryl-4 caprate, polyglyceryl-2 isostearate, etc.

Preferred polyglyceryl di-fatty acid esters are any polyglyceryl-n di-fatty acid esters in which each fatty acid moiety is independently derived from a saturated or unsaturated, straight or branched chain fatty acid containing from 6 to 22 carbon atoms, preferably from 8 to 18 carbon atoms or preferably from 12 to 18 carbon atoms, and most preferably 18 carbon atoms. Preferred compounds are those in which each fatty acid moiety is identical, such as polyglyceryl-3 diisostearate. The polyglyceryl moiety can contain from 2 to 12 glyceryl groups, preferably 3 to 12 groups, more preferably from 3 to 10 groups.

Preferred polyglyceryl di-polyhydroxy fatty acid esters are any polyglyceryl di-polyhydroxy fatty acid esters in which the fatty acid moieties are independently derived from a polyhydroxy saturated or olefinically unsaturated, straight or branched chain fatty acid containing from 6 to 22 carbon atoms, preferably from 8 to 18 carbon atoms, and more preferably 12 to 18 carbon atoms. The polyglyceryl moiety can contain from 2 to 12 glyceryl groups, preferably 3 to 12 groups, more preferably from 3 to 10 groups.

Each polyhydroxy fatty acid moiety can contain from 2 to 8 hydroxy groups. Preferred compounds are those in which each fatty acid moiety is identical.

In a preferred embodiment, the polyglyceryl ester has a HLB (Hydrophile-Lipophile Balance) value from 2 to 22, preferably from 3 to 20, more preferably from 4 to 16.

Aqueous Phase

In an embodiment, the aqueous phase of the cosmetic composition comprises water, such as purified water, deionized water or floral water, and optionally at least one water miscible solvent. According to any one of the inventive embodiments, the aqueous phase may be any cosmetically acceptable water based materials, such as deionized water, purified water or floral water.

Polyol

In an embodiment, the $C_2$-$C_6$ polyol is at least one selected from the group consisting of glycerin, propanediol, butanediol, and sorbitol. The butanediol may be 1,3-butanediol. In an embodiment, the $C_2$-$C_6$ polyol is glycerin.

In an embodiment of the present invention, the cosmetic composition comprises glycerin and sorbitol.

Oil Phase

According to any one of the inventive embodiments, the oil phase may comprise at least one cosmetically or acceptable oil or mixtures thereof. In particular, the oil phase is free from silicone oil and mineral oil.

The oil may be selected from the group consisting of oils of animal or plant origin, synthetic glycerides, fatty esters, fatty alcohols and aliphatic hydrocarbons. These materials may be volatile or non-volatile. Volatile oils may be used in combination with non-volatile oils and/or other wax mentioned in the present description. Suitable oil may be selected from aliphatic hydrocarbons, plant oils, fatty alcohols, esters of fatty alcohols and/or fatty acids other than animal or plant oils and synthetic glycerides, or mixtures thereof. Particularly suitable oil may be selected from the group consisting of plant oils, esters of fatty alcohols, and mixtures thereof.

Suitable plant oils for use in the cosmetic composition of the present invention may nonexclusively include linseed oil, camellia oil, sunflower oil, apricot oil, hazelnut oil, vegetable squalane oil, sasanqua oil, grapeseed oil, peanut oil, coconut oil, palm kernel oil, soybean oil, macadamia nut oil, avocado oil, safflower oil, sweet almond oil, apricot oil, corn oil, jojoba oil, olive oil, sesame oil, palm oil, eucalyptus oil, rosemary oil, lavender oil, pine oil, thyme oil, mint oil, cardamom oil, orange-blossom oil, bran oil, rice oil, rapeseed oil, castor oil, and mixtures thereof.

Suitable animal oils for use in the cosmetic composition of the present invention may nonexclusively include squalene, perhydrosqualene, squalane and mixtures thereof.

Suitable fatty esters or esters of fatty alcohols for use in the cosmetic composition of the present invention may include fatty acid polyglycerides for example diglyceride, triglycerides, preferably triglyceryl esters of saturated and/or unsaturated, branched and/or unbranched alkanecarboxylic acids with a chain length of from 6 to 24, in particular 6 to 18 carbon atoms more preferably triethylhexanoin and caprylic capric triglyceride, dialkyl carbonate such as dioctyl carbonate and dicaprylyl carbonate, diisopropyl sebacate, ethyl laurate, butyl laurate, hexyl laurate, isohexyl laurate, isopropyl laurate, methyl myristate, ethyl myristate, butyl myristate, isobutyl myristate, isopropyl myritate, 2-octyldodecyl myristate, 2-ethylhexyl monococoate (or octyl monococoate), ethyl palmitate, isopropyl palmitate, isobutyl palmitate, 2-ethylhexyl palmitate (or octyl palmitate), butyl stearate, isopropyl stearate, isobutyl stearate, isocetyl stearate, isosteary isostearate, isopropyl isostearate, 2-ethylhexyl stearate (or octyl stearate), decyl oleate, isononyl isononanoate, tridecyl neopentanoate, isocetyl neopentanoate, isostearyl neopentanoate, octyldodecyl neopentanoate and isoarachidyl neopentanoate, and mixtures thereof.

In an embodiment, the suitable oils may be commercially available, for example as MYRITOL® GTEH, MYRITOL® GTEH-SD, MYRITOL® 318 RC, CETIOL® CC, CEGESOFT® PS6, and CEGESOFT® C24 RC, CETIOL® ININ, CETIOL® SN-1 SD, CETIOL® ULTIMATE from. All commercially available (from BASF) cosmetically acceptable oils or mixtures thereof are suitable for use in the compositions of the present invention.

In an embodiment, the cosmetic composition is free or substantially free of polymeric thickener, gelling agent or thickening polymer.

Further Ingredients

In an embodiment, the cosmetic composition may further comprise at least one surfactant selected from the group consisting of anionic surfactant, amphoteric surfactant and cationic surfactant, and mixtures thereof, as long as they are compatible with the above surfactant portion. In an embodiment, based on the total weight of the cosmetic composition, the at least one surfactants selected from the group consisting of anionic surfactant, amphoteric surfactant and cationic surfactant, and mixtures thereof may be present in an amount of from 0.1 to 15% by weight, such as from 0.2 to 14% by weight, from 0.3 to 13% by weight, from 0.4 to 12% by weight, from 0.5 to 11% by weight, from 0.6 to 10% by weight, from 0.7 to 9% by weight, from 0.8 to 8% by weight, from 0.9 to 9% by weight, from 1 to 8% by weight, from 1.1 to 7% by weight, from 1.2 to 6.5% by weight, from 1.3 to 6% by weight, from 1.4 to 5.5% by weight, from 1.5 to 5% by weight, from 1.6 to 4.5% by weight, from 1.7 to 4% by weight, from 1.8 to 3.5% by weight, from 1.9 to 3% by weight.

The compatible anionic surfactants may nonexclusively include alkyl sulphates, alkyl ether sulphates, alkaryl sulphonates, alkanoyl isethionates, alkyl succinates, alkyl sulphosuccinates, N-alkoyl sarcosinates, alkyl phosphates, and alpha-olefin sulphonates, especially their sodium, magnesium ammonium and mono-, di- and tri-thanolamine salts.

The compatible anionic surfactants may be selected from the group consisting of sodium lauryl sulphate, triethanolamine lauryl sulphate, triethanolamine monlauryl phosphate and ammonium lauryl sulphate.

The compatible amphoteric surfactants may nonexclusively include alkyl amine oxides, alkyl betaines, alkyl amidopropyl betaines, alkyl sulphobetaines (sultaines), alkyl glycinates, alkyl carboxyglycinates, alkyl amphopropionates, alkyl amphoglycinates, alkyl amidopropyl hydroxysultaines, acyl taurates and acyl glutamates, wherein the alkyl and acyl groups have from 8 to 19 carbon atoms. Examples include lauryl amine oxide, cocodimethyl sulphopropyl betaine, lauryl betaine, cocamidopropyl betaine and sodium cocamphopropionate.

The compatible cationic surfactants may nonexclusively include quaternary ammonium hydroxides, e.g., tetramethylammonium hydroxide, alkyltrimethylammonium hydroxides wherein the alkyl group has from about 8 to 22 carbon atoms, for example octyltrimethylammonium hydroxide, dodecyltrimethylammonium hydroxide, hexadecyltrimethylammonium hydroxide, cetyltrimethylammonium hydroxide, octyldimethylbenzylammounium hydroxide, decyldimethyl-benzylammonium hydroxide, dioctadecyldimethylammonium hydroxide, tallow trimethylammonium hydroxide, cocotrimetylammonium hydroxide and the corresponding salts thereof containing anions other than hydroxide, e.g., chlorides, cetylpyridinium hydroxide or salts thereof (e.g., chloride), Quaternium-5, Quaternium-31, Quaternium-18, and mixtures thereof.

The cosmetic composition of the present invention may comprise, besides the above-mentioned components, additives generally blended in a cosmetic composition such as moisturizers, antiwrinkle/antiaging agents, cellular stimulants, anti-inflammatory agents, antioxidants, UV absorption/scattering agents, preservatives, pH adjusters, colorants, flavors and the like, as long as the characteristics of the cosmetic composition of the present invention are not impaired.

Suitable moisturizers for use in the cosmetic composition of the present invention may nonexclusively include polyvalent alcohol such as glycerol, 1,3-propanediol, sorbitol and the like; mucopolysaccharides such as sodium hyaluronate, chondroitin sulfate and the like; amino acids such as alanine, sodium pyrrolidonecarboxylate and the like or a salt thereof.

Suitable antiwrinkle/antiaging agents for use in the cosmetic composition of the present invention may nonexclusively include hydrolyzed eggshell membrane, atelocollagen, rice bran extract, rooibos extract and the like.

Suitable cellular stimulants for use in the cosmetic composition of the present invention may nonexclusively include sodium salt of deoxyribonucleic acid, yeast extract, Asian ginseng extract and the like.

Suitable anti-inflammatory agents for use in the cosmetic composition of the present invention may nonexclusively include allantoin, aloe vera extract, krantz aloe extract, chamomile extract, licorice extract, dipotassium glycyrrhizate and the like.

Suitable antioxidants for use in the cosmetic composition of the present invention may nonexclusively include vitamin E such as tocopherol acetate, d-b-tocopherol, dl-α-tocopherol, natural vitamin E and the like; polyphenols such as glucosylrutin, tannic acid and the like; gallic acids such as gallic acid, propyl gallate and the like and a derivative thereof; plant extracts such as Japanese basil leaf extract, sage leaf extract and the like.

Suitable UV absorption/scattering agents for use in the cosmetic composition of the present invention may nonexclusively include methylene bis-benzotriazolyl tetramethylbutylphenol, bis-ethylhexyloxyphenol methoxyphenyl triazine, diethylamino hydroxybenzoyl hexyl benzoate, paradimethylaminobenzoate 2-ethylhexyl, oxybenzone-3-(2-hydroxy-4-methoxybenzophenone), paramethoxycinnamic acid 2-ethylhexyl, 4-tert-butyl-4'-methoxydibenzoylmethane, titanium oxide and the like.

Suitable preservatives for use in the cosmetic composition of the present invention may nonexclusively include sodium benzoate, phenoxyethanol, paraoxybenzoates such as methyl p-hydroxybenzoate, ethyl parahydroxybenzoate, propyl p-hydroxybenzoate and the like.

Suitable pH adjusters for use in the cosmetic composition of the present invention may nonexclusively include succinic acid, citric acid, sodium citrate, tartaric acid, sodium tartarate, sodium hydroxide, potassium hydroxide, triethanolamine, gluconolactone and the like.

Suitable colorants for use in the cosmetic composition of the present invention may nonexclusively include inorganic pigments such as iron blue, ultramarine blue, red iron oxide, black iron oxide, yellow iron oxide, talc, kaolin, manganese violet, carbon black and the like; natural dyes such as β-carotene, lycopene, shisonin, safflor yellow, shikonin, chlorophyll and the like, tar pigments such as red No. 102, red No. 201, Blue No. 202 and the like, lake pigments such as red No. 3 aluminum lake, yellow No. 4 aluminum lake, blue No. 1 barium lake and the like.

Suitable flavors for use in the cosmetic composition of the present invention may nonexclusively include natural flavors such as cinnamon oil, lavender oil, jasmine oil, peppermint oil, orange oil, rose oil and the like; synthetic flavors such as citronellol, eugenol, geraniol, menthol and the like.

The composition of the present invention may also include other additives such as, but not limited to, abrasives, absorbents, a foam building agent, antifoaming agents, antimicrobial agents (e.g., iodopropyl butylcarbamate), biological additives, bulking agents, chelating agents, film formers or materials, e.g., polymers for aiding the film-forming properties of the composition (e.g., copolymer of eicosene and vinyl pyrrolidone), propellants, reducing agents, skin bleaching and lightening agents (e.g., hydroquinone, kojic acid, ascorbic acid, magnesium ascorbyl phosphate, ascorbyl glucosamine), skin soothing and/or healing agents (e.g., panthenol and derivatives (e.g., ethyl panthenol), aloe vera, pantothenic acid and its derivatives, allantoin, bisabolol, silicones, and fatty alcohols.

The above-mentioned additives can be present in the cosmetic composition of the present invention in amounts generally used for cosmetic compositions, as long as the characteristics of the cosmetic composition of the present invention are not impaired.

In a second aspect, the present invention provides a method for preparing the cosmetic composition of the present invention, comprising the following steps:

(a) adding the emulsifier portion, the $C_2$-$C_6$ polyol to the aqueous phase, and mixing—optionally and preferably with heating, stirring or simultaneous heating and stirring them uniformly;
(b) heating the oil phase;
(c) adding the oil phase obtained in step (b) into the aqueous phase obtained in step (a) under stirring; and
(d) cooling the mixture obtained in step (c) under stirring to give a gel.

In an embodiment, the aqueous mixture in step (a) may be heated to a temperature in the range of 50 °C to 80 °C, preferably in the range of 55 °C to 75 °C, more preferably in the range of 60 °C to 70 °C and most preferably in the range of 65 °C to 70 °C.

In an embodiment, the oil phase in step (b) may be heated to a temperature in the range of 50 °C to 80 °C, preferably in the range of 55 °C to 75 °C, more preferably in the range of 60 °C to 70 °C and most preferably in the range of 65 °C to 70 °C.

In an embodiment, in step (c), the adding rate of the oil phase into the aqueous phase may be in the range of from 1 to 8% by weight of the oil phase per minute, such as from 2 to 6% by weight, from 2 to 5% by weight, and from 3 to 5% by weight of the oil phase per minute. The adding rate through the whole adding process may vary depending on the actual situation, while ensuring the uniformly emulsifying. For example, during the early period, the adding rate may be 2% by weight of the oil phase per minute, and during the middle and later periods, the adding rate may be 3 to 5% by weight of the oil phase per minute.

In an embodiment, the stirring of step (c) may be carried out at 200 to 400 rpm.

In an embodiment, the mixture obtained in step (c) may be cooled to the ambient temperature to give a gel.

In a third aspect, the present invention provides use of the cosmetic composition for the preparation of personal care products.

In an embodiment, the personal care products may be one of the following: skin care products, baby care products, hair care products, cleansing products, makeup removers, massage products, bath products, shaving products, cosmetics, tooth pastes, deodorants, anti-perspirants, insect repellants, shampoos, hair conditioners, sun care products, shower gels, hair styling gels, hair anti-dandruff products, hair growth promoter products, hair colorant products, hair bleaching agent products, hair anti-frizzing agent products, hair relaxer products, lubricating gel products, and spermicide gel products.

In a fourth aspect, the present invention provides a method for personal care or cleansing, comprising the step of applying the cosmetic composition of the present invention to a desired location on the skin or hair in the presence of water, and then rinsing off the composition from the skin or hair with water.

In an embodiment, after being applied to the skin or hair, the cosmetic composition of the present invention produces significant amount of cleansing foams.

In an embodiment, the method is a facial cleansing method and preferably a make-up removing method, and the composition is applied to at least one part of the face.

For the purposes of the present invention, the term "personal care" is intended to refer to cosmetic and skin care compositions for application to the skin, including, for example, makeup removers, body washes and cleansers, as well as leave-on application to the skin. In the present invention, the term "personal care" is also intended to refer to hair care compositions including, for example, shampoos, leave-on conditioners, rinse-off conditioners, styling gels, pomades, hair coloring products (e.g., two-part hair dyes), hairsprays, and mousses. Preferably, the personal care composition is cosmetically acceptable. "Cosmetically acceptable" is intended to underscore that materials that are toxic when present in the amounts typically found in personal care compositions are not contemplated as part of the present disclosure.

The aspects of the present invention will become apparent from the specific examples below. It should be understood that the specific examples, while indicating the preferred embodiment of the present invention, are intended for purposes of illustration only and are not intended to limit the scope of the present invention.

Examples

Materials:

- Plantapon® LGC Sorb: Sodium Lauryl Glucose Carboxylate (15-25% by weight), Lauryl Glucoside (10-20% by weight), 35% active (in total) in water, from BASF
- Plantacare® 1200 UP: Lauryl Glucoside, 50% active in water, from BASF
- Lameform® TGI: Polyglyceryl-3 Diisostearate, from BASF
- Poem J-0021: Polyglyceryl-10 Laurate, from Riken Vitamin
- Myritol® GTEH: Triethylhexanoin, from BASF
- Cegesoft® C24: Ethylhexyl Palmitate, from BASF
- Cetiol® SN-1: Cetyl Ethylhexanoate, from BASF
- Cegesoft® PS6: Vegetable Oil, from BASF
- XIAMETER® PMX-0345: Cyclopentasiloxane, Cyclohexasiloxane, from DOWSIL
- Cetiol® CC: Dicaprylyl Carbonate, from BASF
- Eumulgin® 020S: Oleth-20, from BASF

Preparation of Formulations According to the Present Invention and Comparative Formulations The formulations according to the present invention and Comparative formulations were prepared as follows and the weight percentages of the materials are shown in Tables 1 to 8 below:

(a) adding the emulsifier portion, the polyol to the purified water, heating to a temperature of 65 °C, stirring and mixing them uniformly;

(b) heating the oil phase to a temperature of 65 °C;

(c) adding the oil phase obtained in step (b) into the aqueous phase obtained in step (a) under stirring at 300 rpm over 30 minutes, while controlling the adding rate of the oil phase in the range of 2 to 5% by weight of the oil phase per minute; and (d) cooling the mixture obtained in step (c) under stirring to ambient temperature, and thus giving a gel.

TABLE 1

| Ingredients[a] | Formulation 1 (wt % by weight) | Comparative Formulation 1 (% by weight) | Comparative Formulation 2 (% by weight) |
|---|---|---|---|
| Sodium Lauryl Glucose Carboxylate, Lauryl Glucoside (Plantapon ® LGC Sorb, only active accounted) | 3.5 | 5.5 | 0 |
| Polyglyceryl-3 Diisostearate (Lameform ® TGI, 100% active) | 2 | 0 | 5.5 |
| Glycerin | 10 | 6.3 | 10 |
| Water | 6.5 | 10.2 | 6.5 |
| Triethylhexanoin (Myritol ® GTEH) | 78 | 78 | 78 |

[a]Active matter accounted in the formulation

TABLE 2

| Ingredients[a] | Formulation 2 (% by weight) | Comparative Formulation 3 (% by weight) |
|---|---|---|
| Sodium Lauryl Glucose Carboxylate, Lauryl Glucoside (Plantapon ® LGC Sorb, only active accounted) | 4.5 | 0 |
| Polyglyceryl-10 Laurate (Poem J-0021) | 1.0 | 5.5 |
| Glycerin | 10 | 10 |
| Water | 8.4 | 6.5 |
| Triethylhexanoin (Myritol ® GTEH) | 76.1 | 78 |

[a]Active matter accounted in the formulation

TABLE 3

| Ingredients[a] | Formulation 3 (% by weight) | Formulation 4 (% by weight) | Formulation 5 (% by weight) | Formulation 6 (% by weight) |
|---|---|---|---|---|
| Sodium Lauryl Glucose Carboxylate, Lauryl Glucoside (Plantapon ® LGC Sorb, only active accounted) | 4.5 | 4 | 3.6 | 3.3 |
| Polyglyceryl-3 Diisostearate (Lameform ® TGI) | 1.0 | 1.5 | 1.8 | 2.2 |
| Glycerin | 10 | 10 | 10 | 10 |
| Water | 8.4 | 7.5 | 6.7 | 6.5 |
| Triethylhexanoin (Myritol ® GTEH) | 76.1 | 77 | 77.9 | 78 |

[a]Active matter accounted in the formulation

TABLE 4

| Ingredients[a] | Formulation 7 (% by weight) | Formulation 8 (% by weight) | Formulation 9 (% by weight) |
|---|---|---|---|
| Sodium Lauryl Glucose Carboxylate, Lauryl Glucoside (Plantapon ® LGC Sorb, only active accounted) | 5 | 4 | 3.5 |
| Polyglyceryl-10 Laurate (Poem J0021) | 0.55 | 1.5 | 2.0 |
| Glycerin | 10 | 10 | 10 |
| Water | 9.2 | 7.4 | 6.5 |
| Triethylhexanoin (Myritol ® GTEH) | 75.25 | 77.0 | 78.0 |

[a]Active matter accounted in the formulation

TABLE 5

| Ingredients[a] | Form-10 (% by weight) | Form-11 (% by weight) | Form-12 (% by weight) | Form- 13 (% by weight) | Com Form- 4 (% by weight) | Com Form- 5 (% by weight) |
|---|---|---|---|---|---|---|
| Sodium Lauryl Glucose Carboxylate, Lauryl Glucoside (Plantapon ® LGC Sorb, only active accounted) | 2.8 | 2.8 | 2.8 | 2.8 | 2.8 | 2.8 |
| Polyglyceryl-3 Diisostearate (Lameform ® TGI) | 1.6 | 1.6 | 1.6 | 1.6 | 1.6 | 1.6 |
| Glycerin | 8 | 8 | 8 | 8 | 8 | 8 |
| Water | 5.2 | 5.2 | 5.2 | 5.2 | 5.2 | 5.2 |
| Triethylhexanoin (Myritol ® GTEH) | 82.4 | — | — | — | — | — |
| Ethylhexyl Palmitate (Cegesoft ® C24) | — | 82.4 | — | — | — | — |
| Cetyl Ethylhexanoate (Cetiol ® SN-1) | — | — | 82.4 | — | — | — |
| Dicaprylyl Carbonate (Cetiol ®' CC) | — | — | — | 82.4 | — | — |
| Mineral Oil (Mineral oil) | — | — | — | — | 82.4 | — |
| Cyclopentasiloxane, Cyclohexasiloxane (XIAMETER ® PMX-0345) | — | — | — | — | — | 82.4 |

[a]Active matter accounted in the formulation

TABLE 6

| Ingredients[a] | Formulation 14 (% by weight) | Formulation 15 (% by weight) |
|---|---|---|
| Sodium Lauryl Glucose Carboxylate, Lauryl Glucoside (Plantapon ® LGC Sorb, only active accounted) | 2.8 | 2.8 |
| Polyglyceryl-3 Diisostearate (Lameform ® TGI) | 1.6 | 1.6 |
| Glycerin | 8 | 8 |
| Water | 5.2 | 5.2 |
| Triethylhexanoin (Myritol ® GTEH) | 67.4 | 41.2 |
| Vegetable Oil (Cegesoft ® PS6) | 15 | 41.2 |

[a]Active matter accounted in the formulation

TABLE 7

| Ingredients[a] | Formulation 16 (% by weight) |
|---|---|
| Sodium Lauryl Glucose Carboxylate, Lauryl Glucoside (Plantapon ® LGC Sorb, only active accounted) | 2.6 |
| Polyglyceryl-3 Diisostearate (Lameform ® TGI) | 1.5 |
| Glycerin | 7.4 |
| Water | 4.8 |
| Triethylhexanoin (Myritol ® GTEH) | 75.7 |
| 70% Sorbitol | 8 |

[a]Active matter accounted in the formulation

TABLE 8

| Ingredients[a] | Formulation 17 (% by weight) | Comparative Formulation 6 (% by weight) |
|---|---|---|
| Sodium Lauryl Glucose Carboxylate, Lauryl Glucoside (Plantapon ® LGC Sorb, only active accounted) | 2.1 | |
| Lauryl Glucoside (Plantacare ® 1200 UP, 50% active in water) | — | 2.1 |
| Polyglyceryl-3 Diisostearate (Lameform ® TGI) | 1.2 | — |
| Oleth-20 (Eumulgin ® O20S) | — | 1.2 |
| Glycerin | 6.0 | 6.0 |
| Water | 3.9 | 3.9 |
| Dicaprylyl Carbonate (Cetiol ® CC) | 86.8 | 86.8 |

[a]Active matter accounted in the formulation

Evaluation of the Stability of Formulations and Comparative Formulations

The above Formulations and Comparative Formulations were evaluated for the following aspects immediately after preparation and after storage under different storage conditions.

1. Appearance Evaluation

The formulations of Example 1 were observed for the appearance immediately after preparation and after storage at ambient temperature (25 °C), lower temperature (5 °C) and elevated temperature (50 °C) as shown in the following methods A and B respectively:

Method A: stored under ambient temperature (25 °C) for 3 months;

Method B: stored under lower temperature (5 °C) for 3 months; and

Method C: stored under elevated temperature (50 °C) for 1 month.

1.1 Transparence

The transparence of the formulations was evaluated according to the following criteria.

Evaluation criteria

○: transparent;

Δ: somewhat clouded; and

■: remarkably clouded.

1.2 Color Changing

The presence or absence and the level of color changing was observed and evaluated according to the following criteria. Color changing means the transparency of the sample was de-creased when comparing to the initial one.

Evaluation criteria:

○: color changing is not observed;

Δ: color changing is slightly observed; and

■: color changing is remarkably observed.

1.3 Separation

The presence or absence and the level of separation of oil phase and aqueous phase were observed and evaluated according to the following criteria.

Evaluation criteria:

○: separation is not observed;

Δ: separation is slightly observed; and

■: separation is remarkably observed.

TABLE 10

Adjustment of the gel viscosity by additional Sorbitol

| Ingredient | Formulation 10 (% by weight) | Formulation 16 (% by weight) |
|---|---|---|
| Sodium Lauryl Glucose Carboxylate, Lauryl Glucoside (Plantapon ® LGC Sorb, only active accounted) | 2.8 | 2.6 |
| Polyglyceryl-3 Diisostearate (Lameform ® TGI) | 1.6 | 1.5 |
| Glycerin | 8 | 7.4 |
| Water | 5.2 | 4.8 |
| Triethylhexanoin (Myritol ® GTEH) | 82.4 | 75.7 |
| 70% Sorbitol | | 8 |
| Viscosity (mPa · s) | 38,000 | 20,000 |

The addition of sorbitol into the cosmetic composition of the present invention de-creases the viscosity while the excellent transparency and stability are not affected.

Make-Up Cleansing Test

A Make-Up Removal In-Vitro Test was Conducted as Follows:

PMMA board with coarse surface was used to mimic human skin surface. After both sides of the board were cleaned with ethanol and get dried①, 100 mg of each

TABLE 9

| | Immediately after preparation | | | Method A (25° C., 3 months) | | | Method B (5° C., 3 month) | | | Method C (50° C., 1 month) | | |
|---|---|---|---|---|---|---|---|---|---|---|---|---|
| | Trans.[1] | Col.[2] | Sep.[3] | Trans.[1] | Col.[2] | Sep.[3] | Trans.[1] | Col.[2] | Sep.[3] | Trans.[1] | Col.[2] | Sep.[3] |
| Formulation 1 | ○ | ○ | ○ | ○ | ○ | ○ | ○ | ○ | ○ | ○ | ○ | ○ |
| Formulation 2 | ○ | ○ | ○ | ○ | ○ | ○ | ○ | ○ | ○ | ○ | ○ | ○ |
| Formulation 3 | ○ | ○ | ○ | ○ | ○ | ○ | ○ | ○ | ○ | ○ | ○ | ○ |
| Formulation 4 | ○ | ○ | ○ | ○ | ○ | ○ | ○ | ○ | ○ | ○ | ○ | ○ |
| Formulation 5 | ○ | ○ | ○ | ○ | ○ | ○ | ○ | ○ | ○ | ○ | ○ | ○ |
| Formulation 6 | ○ | ○ | ○ | ○ | ○ | ○ | ○ | ○ | ○ | ○ | ○ | ○ |
| Formulation 7 | ○ | ○ | ○ | ○ | ○ | ○ | ○ | ○ | ○ | ○ | ○ | ○ |
| Formulation 8 | ○ | ○ | ○ | ○ | ○ | ○ | ○ | ○ | ○ | ○ | ○ | ○ |
| Formulation 9 | ○ | ○ | ○ | ○ | ○ | ○ | ○ | ○ | ○ | ○ | ○ | ○ |
| Formulation 10 | ○ | ○ | ○ | ○ | ○ | ○ | ○ | ○ | ○ | ○ | ○ | ○ |
| Formulation 11 | ○ | ○ | ○ | ○ | ○ | ○ | ○ | ○ | ○ | ○ | ○ | ○ |
| Formulation 12 | ○ | ○ | ○ | ○ | ○ | ○ | ○ | ○ | ○ | ○ | ○ | ○ |
| Formulation 13 | ○ | ○ | ○ | ○ | ○ | ○ | ○ | ○ | ○ | ○ | ○ | ○ |
| Formulation 14 | ○ | ○ | ○ | ○ | ○ | ○ | ○ | ○ | ○ | ○ | ○ | ○ |
| Formulation 15 | ○ | ○ | ○ | ○ | ○ | ○ | ○ | ○ | ○ | ○ | ○ | ○ |
| Formulation 16 | ○ | ○ | ○ | ○ | ○ | ○ | ○ | ○ | ○ | ○ | ○ | ○ |
| Formulation 17 | ○ | ○ | ○ | ○ | ○ | ○ | ○ | ○ | ○ | ○ | ○ | ○ |
| Comparative Formulation 1 | ■ | ○ | ○ | ■ | ○ | ○ | ■ | ○ | ○ | ■ | ■ | Δ |
| Comparative Formulation 2 | | | ■ | | | | | | | | | |
| Comparative Formulation 3 | ■ | ○ | ○ | ■ | ○ | ○ | ■ | ○ | ○ | ■ | ■ | ○ |
| Comparative Formulation 4 | ■ | ○ | ○ | ■ | ○ | ○ | ■ | ○ | ○ | ■ | ○ | ○ |
| Comparative Formulation 5 | ■ | ○ | ○ | ■ | ○ | ○ | ■ | ○ | ○ | ■ | ○ | ○ |
| Comparative Formulation 6 | ○ | ○ | ○ | ○ | ○ | ○ | ○ | ○ | ○ | ○ | ○ | ○ |

Note:
[1]transparence,
[2]color changing;
[3]separation.

The test results illustrate that the inventive formulations can achieve satisfied transparency and excellent stability.

Viscosity Measurement

The viscosity in mPa·s was determined by rotational method and obtained at 23 °C using a Brookfield viscometer DV2T (spindle #7, rotational speed as 10 rpm).

makeup products (Lip stick: M.A.C Lipstick Ruby Woo; Foundation: L'Oreal Paris foundation Infallible stay fresh 24 h; Mascara: Kissme waterproof mascara) was applied in circles with a diameter of 7 cm on the coarse surface of PMMA board, the makeup products were evenly distributed by finger with glove. After waiting for 30 min②, 200 ml of makeup remover product was evenly applied on each circle with makeup products, the products were evenly distributed by finger with glove, each area was distributed for 65 circles. Then, add 200 uL deionized water onto the test circle and distribute with gloves for 20 circles. Repeat this step once. Finally, added 2.00 g deionized water onto cotton pads, and used a draw down device to push the wet cotton pads passing through the test areas for twice to remove the residue③. Pictures were taken in a standardized demo chamber on the three time points: ①Before applying makeup products (TO); ②Before applying makeup remover products (T1); ③After using draw down device to remove the residue (T2). Software was used to assess the grey level for each time points, and calculate make-up removal efficacy % as the result with the formula: Removal efficacy (ΔGrey value %)=(T2−T1)/(T0−T1)×100%.

Test formulation was set as below, Formulation 17 is free from ethoxylated emulsifier, whiling Comparative Formulation 6 uses ethoxylated-containing emulsifier. The test results show that both formulations demonstrate excellent make-up removal efficacy.

TABLE 11

| Ingredients[a] | Formulation 17 (% by weight) | Comparative Formulation 6 (% by weight) |
|---|---|---|
| Sodium Lauryl Glucose Carboxylate, Lauryl Glucoside (Plantapon ® LGC Sorb, only active accounted) | 2.1 | |
| Lauryl Glucoside (Plantacare ® 1200 UP, 50% active in water) | — | 2.1 |
| Polyglyceryl-3 Diisostearate (Lameform ® TGI) | 1.2 | — |
| Oleth-20 (Eumulgin ® O20S) | — | 1.2 |
| Glycerin | 6.0 | 6.0 |
| Water | 3.9 | 3.9 |
| Dicaprylyl Carbonate (Cetiol ® CC) | 86.8 | 86.8 |

[a]active matter accounted in the formulation

TABLE 12

| | Lip stick (ΔGrey value %) | Foundation (ΔGrey value %) | Mascara (ΔGrey value %) |
|---|---|---|---|
| Formulation 17 | 66.29 ± 2.25 | 75.17 ± 3.24 | 80.29 ± 1.24 |
| Comparative Formulation 6 | 49.91 ± 2.86 | 79.73 ± 3.06 | 54.45 ± 2.45 |

In-vitro make up removal test results (ΔGrey value %) were showed, higher value means better efficacy. From the results, Formulation 17 without use of ethoxylated emulsifier has significantly better make-up removal performance on lip stick and mascara product and comparable efficacy was found on foundation removal test.

The invention claimed is:

1. A cosmetic composition, comprising (a) an oil phase;

(b) an emulsifier portion comprising at least one carboxylated alkyl polyglycoside, at least one alkyl polyglycoside, and at least one polyglyceryl ester;

(c) an aqueous phase; and (d) at least one $C_2$-$C_6$ polyol;

wherein said composition is in a form of a transparent gel, and wherein an oil phase is free from mineral oil and silicone oil.

2. The cosmetic composition of claim 1, wherein based on the total weight of the composition, (1) the oil phase is present in an amount of from 50 to 90% by weight;

(2) the emulsifier portion comprising at least one carboxylated alkyl polyglycoside, at least one alkyl polyglycoside, and at least one polyglycerol ester is present in an amount of from 1 to 20% by weight;

(3) the aqueous phase is present in an amount of from 1 to 15% by weight; and (4) the at least one $C_2$-$C_6$ polyol is present in an amount of from 1 to 15% by weight.

3. The cosmetic composition of claim 1, wherein the at least one carboxylated alkyl polyglycoside and the at least one alkyl polyglycoside are present at a weight ratio in the range of 1:6 to 6:1.

4. The cosmetic composition of claim 1, wherein, in the emulsifier portion, the emulsifiers are present at a weight ratio of a sum of the at least one carboxylated alkyl polyglycoside and the at least one alkyl polyglycoside to the at least one polyglyceryl ester in the range of 9:1 to 1:9.

5. The cosmetic composition of claim 1, wherein the cosmetic composition has a viscosity at 25 °C of from 5,000 to 500,000 mPas.

6. The cosmetic composition of claim 1, wherein the alkyl polyglycoside is of a formula (I):

$$R_1—O—(R_2—O)_a—(Z)_b—H \quad (I)$$

wherein $R_1$ is a straight chain or branched $C_6$-$C_{24}$-hydrocarbyl, $R_2$ is a straight chain $C_2$-$C_4$-alkylene, a is a number in a range of 0 to 10, Z is a residue of a reducing sugar having 5 to 6 carbons, and b is a number in the range of 1 to 5.

7. The cosmetic composition of claim 1, wherein the carboxylated alkyl polyglycoside is of a formula (II):

$$R_3—O—(R_4—O)_m—(S)_n—CH_2COO^-X^+ \quad (II)$$

wherein $R_3$ is a straight chain or branched $C_6$-$C_{24}$-hydrocarbyl, $R_4$ is straight chain $C_2$-$C_4$-alkylene, m is a number in a range of 0 to 10

S is a residue of a reducing sugar having 5 to 6 carbons, and n is a number in a range of 1 to 5, and X is an alkali metal ion.

8. The cosmetic composition of claim 1, wherein the polyglyceryl ester is at least one selected from the group consisting of polyglycerin fatty acid ester, polyglyceryl di-fatty acid ester, and polyglyceryl di-polyhydroxy fatty acid ester.

9. The cosmetic composition of claim 1, wherein the $C_2$-$C_6$ polyol is one or more selected from the group consisting of glycerin, propanediol, butanediol, and sorbitol.

10. The cosmetic composition of claim 1, wherein the composition is free or substantially free from an ethoxylated emulsifier.

11. The cosmetic composition of claim 1, wherein the oil phase comprises one or more cosmetically acceptable oils or mixtures thereof selected from the group consisting of oils of animal or plant origin, synthetic glycerides, fatty esters, fatty alcohols, and aliphatic hydrocarbons.

12. The cosmetic composition claim 1, wherein the composition is free or substantially free of a polymeric thickener or a gelling agent or a thickening polymer.

13. A method for preparing the cosmetic composition of claim 1, comprising:

(a) adding the emulsifier portion, and the $C_2$-$C_6$ polyol to the aqueous phase, and mixing, optionally with heating, stirring, or simultaneous heating and stirring them uniformly;

(b) heating the oil phase;

(c) adding the oil phase obtained in step (b) into the aqueous phase obtained in step (a) under stirring; and (d) cooling the mixture obtained in step (c) under stirring to give a gel.

14. The cosmetic composition of claim 1 wherein the cosmetic composition is a personal care product selected from the group consisting of skin care products, baby care products, hair care products, cleansing products, makeup removers, massage products, bath products, shaving products, cosmetics, tooth pastes, deodorants, anti-perspirants, insect repellants, shampoos, hair conditioners, sun care products, shower gels, hair styling gels, hair anti-dandruff products, hair growth promoter products, hair colorant products, hair bleaching agent products, hair anti-frizzing agent products, hair relaxer products, lubricating gel products, and spermicide gel products.

15. A method for personal care or cleansing, comprising applying the cosmetic composition of claim 1 to a desired location on skin or hair in the presence of water, and then rinsing off the composition from the skin or hair with water.

16. The method of claim 15, wherein after being applied to the skin, the composition produces a cleansing foam.

17. The method of claim 15, wherein the method is a facial cleansing method or a make-up removing method and the composition is applied to at least one part of the face.

* * * * *